United States Patent [19]
Bauer et al.

[11] Patent Number: 5,959,108
[45] Date of Patent: Sep. 28, 1999

[54] METHOD FOR PREPARING A CRYSTALLINE POLYMORPH OF TERAZOSIN MONOHYDROCHLORIDE

[75] Inventors: Christophe Bauer, Strasbourg; Jean-Marie Grunenwald, Kertzfeld, both of France

[73] Assignee: Cu Chemie Uetikon GmbH, Germany

[21] Appl. No.: 09/095,483

[22] Filed: Jun. 10, 1998

Related U.S. Application Data

[63] Continuation-in-part of application No. PCT/EP96/05570, Dec. 12, 1996.

[30] Foreign Application Priority Data

Dec. 13, 1995 [DE] Germany ............ 195 46 573

[51] Int. Cl.⁶ .................................. C07D 241/04
[52] U.S. Cl. ........................................ 544/291
[58] Field of Search ............................. 544/291

[56] References Cited

U.S. PATENT DOCUMENTS

| | | | |
|---|---|---|---|
| 5,294,615 | 3/1994 | Meyer et al. | 544/291 X |
| 5,362,730 | 11/1994 | Bauer et al. | 544/291 X |
| 5,412,095 | 5/1995 | Morley et al. | 544/291 |
| 5,504,207 | 4/1996 | Mannino et al. | 544/291 |
| 5,587,377 | 12/1996 | Patel et al. | 544/291 X |

FOREIGN PATENT DOCUMENTS 0683167  11/1995  European Pat. Off. .

OTHER PUBLICATIONS

Chem. Abstracts, vol. 119, No. 28, 1993.

*Primary Examiner*—Michael G. Ambrose
*Attorney, Agent, or Firm*—Bierman, Muserlian and Lucas

[57] ABSTRACT

A crystalline polymorphous terazosine monohydrochloride is obtained by suspending and treating a crystalline addition product of terazosine hydrochloride and methanol in a polar solvent which is an alcohol with 2 to 6 carbon atoms or a ketone with 2 to 6 carbon atoms or a mixture thereof. The thus obtained crystalline polymorphous terazosine hydrochloride is characterized by a reduced hygroscopicity and solvent residue retention capacity.

4 Claims, 1 Drawing Sheet

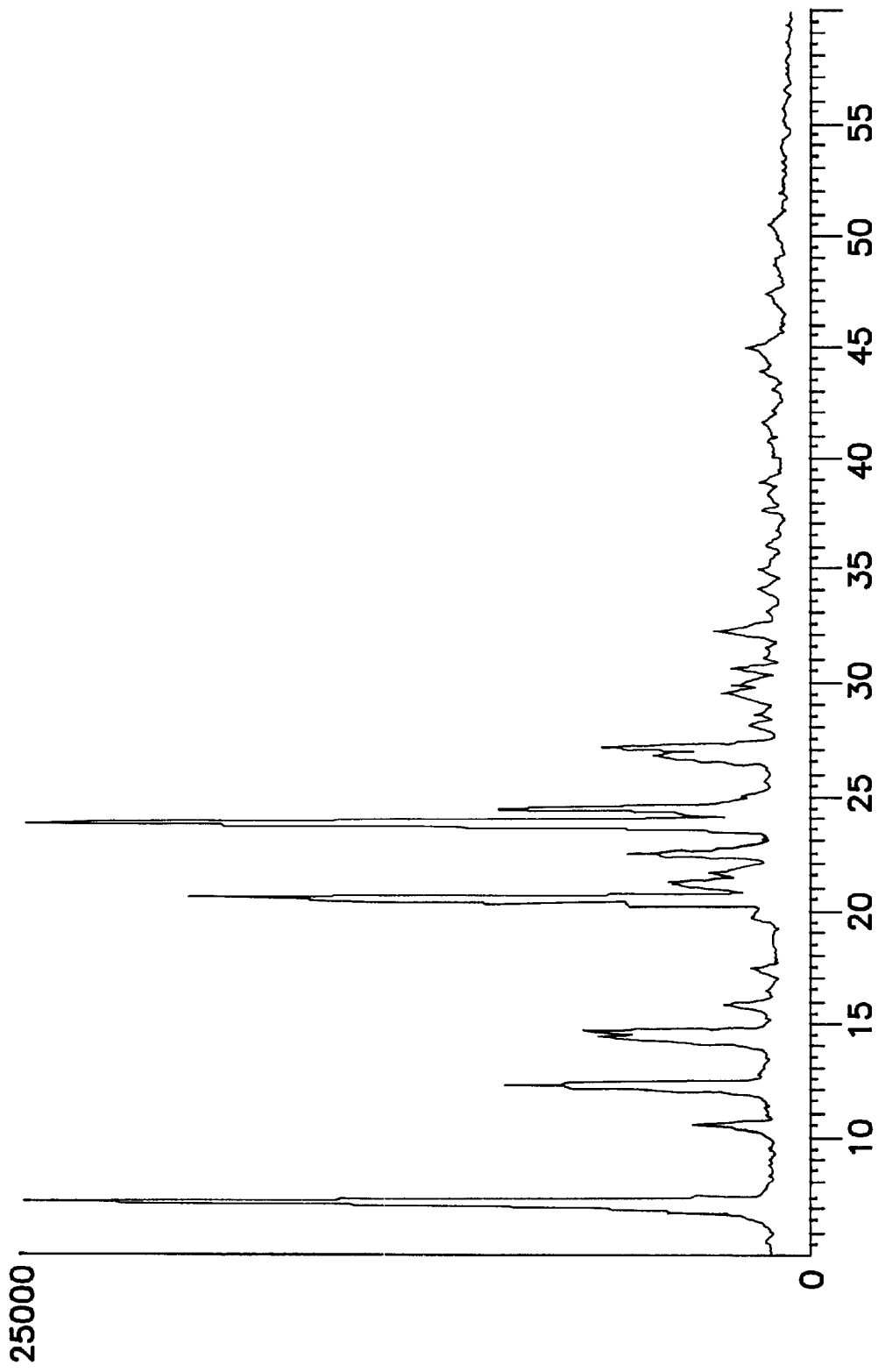

METHOD FOR PREPARING A CRYSTALLINE POLYMORPH OF TERAZOSIN MONOHYDROCHLORIDE

CROSS REFERENCE TO RELATED APPLICATIONS

This is a Continuation-in-part of International Application PCT/EP96/05570, with an international filing date of Dec. 12, 1996.

BACKGROUND OF THE INVENTION

1. Field of the Invention

The Invention relates to a method for preparing a crystalline polymorph of 1-(4-amino-6,7-dimethoxy-2-quinazolinyl)-4-(2-tetrahydrofuroyl)-piperazine-monohydrochloride, hereinafter abbreviated as terazosin hydrochloride.

2. Description of Related Art

The compound 1-(4-amino-6,7-dimethoxy-2-guinazolinyl)-4-(2-tetrahydrofuroyl)-piperazine is generally known under the name terazosin. For the monohydrochloride of this compound there have been known to exist a plurality of anhydrous crystalline modifications (polymorphs) as well as a crystalline dihydrate form and a crystalline adduct with methanol. The compound and the different polymorphs thereof are suitable for pharmaceutical use, for example for the treatment of hypertension.

The Japanese Laid-Open Unexamined Patent Application 05-78352 SUMIKA describes a plurality of crystalline forms of terazosin hydrochloride and the ways of preparing them. One crystalline polymorph, denoted as type A-2 in that document, is characterized by an X-ray powder diffraction pattern having characteristic peaks at 7°, 12°, 20.3° and is believed to be identical to the product of the method according to the present Invention. According to the prior art document this polymorph is prepared as follows: First the free terazosin base is prepared. This is converted into the crystalline adduct of the hydrochloride thereof with methanol. Thereafter, the methanol included in the crystal is removed by drying, which necessitates temperatures around 110° C. One obtains a substantially methanol free compound, which is very hygroscopic. This is further treated with ethanol or mixtures of ethanol and methylene chloride for obtaining the desired crystalline polymorph which is substantially not hygroscopic.

U.S. Pat. No. 5,412,095 and EP 0 683 167 disclose methods for obtaining other crystalline forms of terazosin-hydrochloride. One of the methods described therein also comprises the treatment of the adduct of terazosin-hydrochloride and methanol in suspension in a solvent such as ethanol. This prior art treatment, however, is performed at a comparatively low temperature (50° C.) and for a comparatively short time (10 minutes or 30 minutes), and the product is a crystalline polymorph, designated as Form III in this document, which differs from the polymorph according to the Invention with respect to its X-ray pattern and other parameters.

The crystalline polymorph to which the present Invention relates is also described in EP-0 708 104 A1 which is not prepublished, and it is designated there as "Form IV". The method of preparation proposed in this document starts from N-(2-tetrahydrofuroyl)-piperazine (the preparation of which by hydrogenation of N-(2-furoyl)-piperazine has already been known from U.S. Pat. No. 4,026,894), which is then coupled with 4-amino-2-chloro-6,7-dimethoxy-quinazoline, which requires a treatment including boiling for several hours in a solvent having a high boiling temperature, whereby terazosin hydrochloride in the crystalline Form IV is obtained. This product is then converted into the dihydrate and dried. A drawback of this method consists in requiring several hours of boiling in a solvent having a high boiling temperature (for example methoxyethanol which is objectionable for health reasons) whereby impurities are necessarily formed and an undesirable dark color is obtained. Thus, the crystalline Form IV is not obtained in the optimal purity which is desired for pharmacological uses, but requires further treatment (forming of dihydrate), which causes a purification, including a treatment with diatomaceous earth.

Other crystalline polymorphs of terazosin hydrochloride and methods for their preparation are disclosed in U.S. Pat. Nos. 5,294,615, 5,362,730 and 5,412,095 and are referred therein as Form II and Form III, respectively, and are characterized by the characteristic peaks of the X-ray powder diffraction patterns thereof.

SUMMARY OF THE INVENTION

It is an object of the Invention to provide a novel method of preparing the crystalline polymorph of terazosin hydrochloride previously known under the designations A-2 and Form IV, which enables to obtain this crystalline polymorph in a simple process and with high purity.

The method according to the Invention starts from the stable crystalline adduct of terazosin hydrochloride and methanol which is then treated with organic polar solvents or solvent mixtures from the group of alcohols and ketones, without preliminary intermediate drying. It has been found that the methanol-wet methanol adduct, as it is obtained in the preparation of the adduct, can be used without disadvantages, and that the residual methanol content of the final product is in a range acceptable for pharmacological use. According to the Invention it has surprisingly been found that by selecting a suitably higher temperature and treatment time the polymorph Form IV is obtained, rather than the aforementioned polymorph Form III or any other known polymorph (Form I or Form II).

A substantial advantage of the method according to the Invention as compared with the above-mentioned known from JP-A-05-78352 consists in eliminating the intermediate drying step at temperatures around 110° C. This intermediate drying step of the prior art method has two substantial disadvantages. On the one hand the drying results in a very hygroscopic product. On the other hand the treatment at the drying temperature over several hours results in a thermic load which can cause the product to decompose and impurities to be generated, which is very undesirable when using the product as a pharmaceutical active ingredient. These disadvantages are avoided by the method according to the present Invention.

The polymorph prepared by the method according to the present Invention has substantial advantages over other anhydrous polymorphs of terazosin hydrochloride. It is characterized by a very low hygroscopicity as well as a low retention for residual solvents, which is a substantial advantage with respect to the use as a pharmaceutical active ingredient.

BRIEF DESCRIPTION OF THE DRAWING

In the accompanying drawings, constituting a part hereof, and in which like reference characters indicate like parts, FIG. 1 illustrates an X-ray powder diffraction pattern of the crystalline polymorph.

DETAILED DESCRIPTION OF THE INVENTION

A preferred embodiment of the method according to the present Invention is described hereinafter.

1. Preparation of the Crystalline Adduct of Terazosin Hydrochloride and Methanol 37.6 g 4-amino-2-(1-piperazinyl)-6,7-dimethoxyquinazoline and 15.8 g triethylamine are suspended in 400 ml methylene chloride. The suspension is cooled to −5° C. This suspension is stirred while 21.0 g tetrahydrofuran-2-carboxylic acid chloride are added drop by drop. The suspension is continued to be stirred for two hours at 0° C., thereafter the solvent is distilled off under vacuum. 200 ml methanol and 200 ml acetone are added to the residue. The resulting suspension is kept under reflux for 0.5 hours while stirring. Thereafter, it is cooled to 0° C. The product is isolated by filtration. 78 g of moist terazosin base are obtained.

This terazosin base is suspended in 400 ml methanol and 400 ml methylene chloride. While stirring, 23.8 g of a 20% solution of hydrochloric acid in methanol are added drop by drop. One obtains a solution which is filtered to become clear. The methylene chloride is selectively distilled off under vacuum which causes precipitation of the product. The suspension is continued to be stirred for 3 hours at room temperature, thereafter the product is isolated by filtration. One obtains 74 g of moist terazosin hydrochloride methanol adduct which may be dried at 50° C. under vacuum, if desired. One obtains 49.0 g of a white crystalline powder containing ca. 1 mol methanol per mol terazosin hydrochloride. A further purification of the methanol adduct is possible by re-crystallization from methanol.

The method steps as described so far correspond in principle to a method known from the above mentioned JP-A-05-78352 for preparing the methanol adduct which is designated as "Type M" in this document.

2. Preparation of the Crystalline Polymorph 10 g of the crystalline adduct, the preparation of which has been described above, are suspended in 100 ml ethanol denatured with 2-butanone. The suspension is heated under reflux and is kept for two hours at the reflux of the ethanol, the reflux temperature being optionally in the range of 78° C. to 80° C., or higher. Thereafter the suspension is cooled to 20° C. The product is isolated by filtration and dried at 50° C. under vacuum. One obtains 8.4 g crystalline powder, and the X-ray powder diffraction pattern of this product is shown in the drawing, FIG. 1. A determination of the contents of residual solvents shows that the crystalline powder typically contains less than 100 ppm methanol and less than 100 ppm ethanol.

The methanolate of the terazosin monohydrochloride, which is to be treated with the polar solvent, is soluble in the polar solvent only to a very small degree. The amount of the polar solvent used is selected so that the amount of methonalate which is solved in the solvent is as small as possible. Thus, almost the entire amount of the product to be treated will be suspended in the polar solvent. This provides substantial advantages for performing the method, especially for the retrieval of the solid product by simple mechanical separation such as filtration. The treatment in polar solvent is preferably carried out at an elevated temperature.

The crystalline form of the product obtained by the method according to the Invention is characterized by the X-ray powder diffraction pattern as shown in the drawing. This pattern has characteristic peaks as the following values expressed in degrees of angle of 2 θ: 7.04; 10.30; 12.02; 14.12; 14.44; 20.34; 22.34; 22.62; 23.58; 24.28 and 26.96, all values within a tolerance of ±0.2.

The Invention is not limited to the details of the example described above. For example, the polar solvent for treating the crystalline methonalate of terazosin hydrochloride can be any solvent selected from the group of alcohols having two to six carbon atoms or ketones having two to six carbon atoms or a mixture of two or more of these solvents.

Moreover, the Invention is not limited to the temperature and time for treating the crystalline adduct of terazosin-hydrochloride and methanol as set forth in the examples. Within the teaching of this Invention the person skilled in the art can easily find out other ranges of temperature and/or treatment time, in relation to the particular solvent used, that are sufficient and suitable for the desired crystalline polymorph known as Form IV, to be formed in the reflux of the solvent.

Further examples of suitable ranges of temperature and treatment time for the treatment of the methanol adduct of terazosin-hydrochloride in the reflux of a polar solvent in a method according to the Invention, whereby the desired crystal polymorph Form IV is obtained, are the following:

treatment in ethanol at 60° C.–70° C. for 1–4 hours;

treatment in ethanol at 85° C.–130° C. for 1–4 hours under pressure in an autoclave;

treatment in isopropanol at 70° C.–130° C. for 1–4 hours, if necessary under pressure;

treatment in isopentanol at 80° C.–130° C. for 0.5–4 hours.

Although only a limited number of specific embodiments of the present Invention have been expressly disclosed, it is, nonetheless, to be broadly construed and not to be limited except by the character of the claims appended hereto.

What we claim is:

1. A method for preparing a crystalline anhydrous polymorph of 1-(4-amino-6,7-dimethoxy-2-quinazolinyl)-4-(2-tetrahydrofuroyl)-piperazine-monohydrochloride (terazosin monohydrochloride), of crystalline Form IV which has an X-ray powder diffraction pattern with characteristic peaks at the following values of 2 θ (in degrees): 7.04; 10.30; 12.02; 14.12; 14.44; 20.34; 22.34; 22.62; 23.58; 26.96, each value ±0.2, comprising the following steps:

preparation of the crystalline adduct of terazosin monohydrochloride and methanol;

treatment of said crystalline adduct in suspension in a polar solvent selected from the group of alcohols having two to six carbon atoms, ketones having three to six carbon atoms and a mixture thereof, separation of the solid product from said suspension, said treatment in suspension being performed at an elevated temperature of not less than 60° C., and for a time period which is not less than 0.5 hours if said temperature is at least 80° C., and not less than 1 hour if said temperature is less than 80° C., said temperature and the time period being selected to be sufficiently high for said crystalline Form IV to be formed.

2. The method as claimed in claim 1 wherein said treatment is performed under reflux of said polar solvent at said elevated temperature.

3. The method as claimed in claim 1 wherein said treatment in suspension in the polar solvent is performed for a time period of at least one hour.

4. The method as claimed in claim 3 wherein the treatment is performed for about 2 hours.

* * * * *